United States Patent [19]

Charoy et al.

[11] Patent Number: 4,947,132
[45] Date of Patent: Aug. 7, 1990

[54] METHOD FOR DETECTING THICKNESS VARIATIONS IN THE WALL OF A TUBULAR BODY WHICH CONDUCTS ELECTRICITY

[75] Inventors: Alain Charoy, Echirolles, France; Jacques Vermot-Gaud, Perly, Switzerland; Jean-Louis Prost, Geneva, Switzerland; Michel Kornmann, Grand Lancy, Switzerland; Dieter Gold, Voiron, France

[73] Assignee: Battelle Memorial Institute, Geneva, Switzerland

[21] Appl. No.: 236,227

[22] PCT Filed: Nov. 18, 1987

[86] PCT No.: PCT/CH87/00153
§ 371 Date: Jul. 25, 1988
§ 102(e) Date: Jul. 25, 1988

[87] PCT Pub. No.: WO88/04028
PCT Pub. Date: Jun. 2, 1988

[30] Foreign Application Priority Data
Nov. 25, 1986 [CH] Switzerland .................. 4710/86

[51] Int. Cl.⁵ .............................................. G01R 27/16
[52] U.S. Cl. ..................................... 324/699; 324/700
[58] Field of Search ................. 324/65 CR, 64, 57 R, 324/522, 523, 525

[56] References Cited

U.S. PATENT DOCUMENTS

| 2,124,577 | 7/1938 | Knerr . | |
|---|---|---|---|
| 2,593,175 | 4/1952 | Packard et al. | 324/57 R |
| 3,636,441 | 1/1972 | Fujimura et al. | 324/64 |
| 3,786,349 | 1/1974 | Devenyi | 324/57 R |
| 4,048,558 | 9/1977 | Goodman | 324/57 R |
| 4,189,778 | 2/1980 | Vogel | 324/57 R |
| 4,683,419 | 7/1987 | Neuelmann et al. | 324/64 |

FOREIGN PATENT DOCUMENTS

| 175257 | 3/1986 | European Pat. Off. . | |
|---|---|---|---|
| 159274 | 3/1983 | Fed. Rep. of Germany | 324/64 |
| 2287693 | 5/1976 | France | 324/64 |
| 840552 | 7/1960 | United Kingdom . | |
| 952106 | 3/1964 | United Kingdom . | |
| 2161936 | 1/1986 | United Kingdom . | |

OTHER PUBLICATIONS

"The General Radio Experimenter", vol. 30, No. 11, Apr. 1956, A High Precision Impedance Comparator.
Industrial Laboratory, vol. 42, No. 2, pp. 292–295, 2/1976, Markochev et al., "Measurement Rate of Supercritical Crack Growth by Method of Potential Difference".

Primary Examiner—Reinhard J. Eisenzopf
Assistant Examiner—Maura K. Regan
Attorney, Agent, or Firm—Cushman, Darby & Cushman

[57] ABSTRACT

The method is based on the exploitation of the "skin effect" occuring in any current-conducting material as a function of the current frequency going through said material. A transformer (5) is supplied from a generator (2) and an amplifier (4) to produce the current intended to supply the tube (T) and to measure the voltage at the terminals of a shunt (6). This voltage which is characteristical of the energization current is amplified by an amplifier (8) and brought to the reference input of a phase correlation amplifier (1). The resistive component of the signal on the tube is then measured by said amplifier (1) by just measuring the signal phase component.

4 Claims, 3 Drawing Sheets

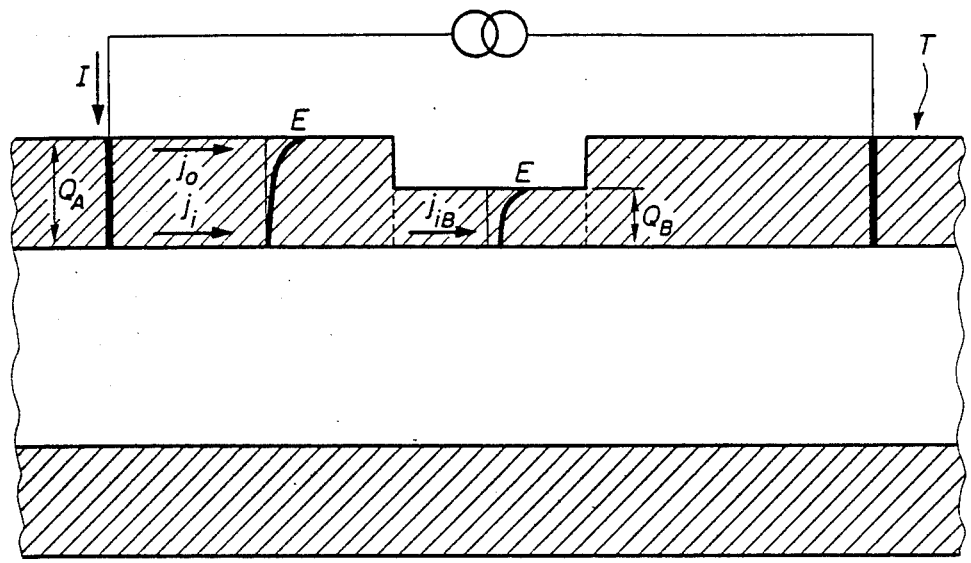
FIG. 1
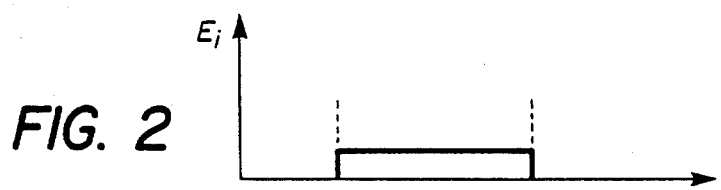
FIG. 2
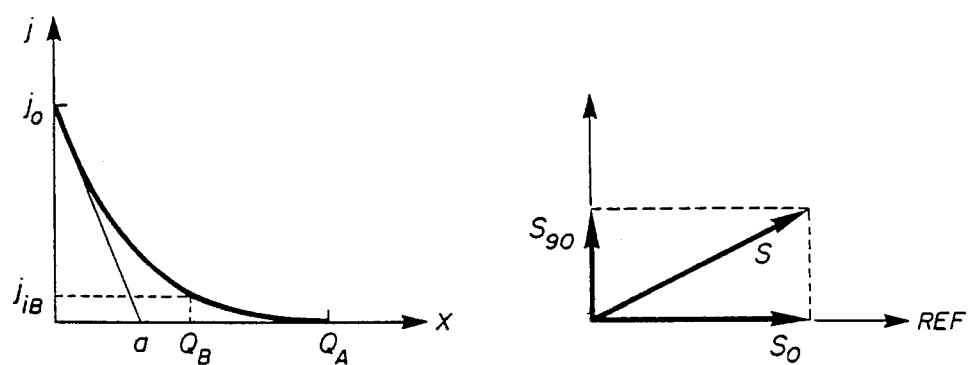
FIG. 3
FIG. 4

METHOD FOR DETECTING THICKNESS VARIATIONS IN THE WALL OF A TUBULAR BODY WHICH CONDUCTS ELECTRICITY

The present invention relates to a method for detecting thickness variations in the wall of a tubular body made of a material which is a conductor of electricity.

The problem of detecting corrosion of pipes arises not only in the case of buried pipes wherein the corrosion appears on the external face, but also in the case of pipes in which corrosive substances circulate, producing a corrosion on the internal face. In one or the other case, it is not possible to perform in a simple manner a visual inspection of the state of the pipes. That is the reason why different methods have been proposed, based on the measuring of magnetic or electrical parameters, which enable the obtaining of characteristic signals showing the state of corrosion of the pipe wall.

It has already been proposed in U.S. Pat. No. 4,048,558 to detect the existence of defects in the wall of a tube by using the "skin effect" whose depth is dependent upon the current frequency. This process consists in supplying a face of a tube with currents of different frequencies, and in measuring the impedance variation of this tube, in dependence upon the frequency. Each of these measurements is compared either to another section of the same tube, maintained at a temperature equal to that of the section of tube to be measured, or to a reference tube. This manner of proceeding makes it possible to dispense with parameters of resistivity and of permeability $\rho$ and $\mu$ which are dependent upon the metal of the tube and upon its temperature, so that the variations which will appear during the course of the comparison will necessarily be due to differences in the structure of the wall of the two compared tube sections. This manner of proceeding necessitates having, in the sample and in the reference pipe, the same values for $\rho$ and $\mu$. This is not possible in the case of a buried pipe, it being given that one cannot reproduce on a reference pipe the same conditions as those in the buried pipe. Consequently, in that case, it is not only the possible defects which are unknown, but also the parameters $\rho$ and $\mu$.

The EP-0.175.257 has also proposed the detecting of defects on tubular conductors by using the skin effect. According to this method, the tubular conductor is supplied with alternating current of a determined frequency, in a given direction, generating a magnetic flux with a given direction, a voltage drop is picked up through two measuring points which are spaced apart from each other by a distance given with two measurement lines touching the tubular conductor, a first conducting loop is formed, from the measurement lines and the tubular conductor, with a useful induction surface which is as small as possible, a second conducting loop is formed, parallel to the direction of the current and perpendicular to that of the magnetic flux, with this second loop there is measured an induced voltage due to the change of magnetic flux, as near as possible to the measuring points, the voltage drop and the induced voltage are fed into an electronic evaluation circuit for measuring the voltage drop, and from the voltage drop and the induced voltage there is deduced the local resistance of the tubular conductor between the measuring points.

This method is not adapted for the measuring of defects on pipe segments several metres long, and for this reason, it necessitates having access to the tubular conductor over its entire length, since it necessitates a sort of auscultation of the external face of the conductor, and it only enables the measurement of very short segments, the auscultation device requiring to be moved along the tubular conductor.

In the case of buried pipes, the electrical measurements are rendered difficult and inaccurate, due to the influences of the earth which covers the pipe. That is the reason why it has also been proposed to mount the entirety of the apparatuses, for measuring and recording these measurements, on a mobile support which is intended to be introduced into the pipe and to be displaced there, drawn along either by the flow of fluid in the pipe, or by independent propulsion means. This technique, which utilizes measurement methods such as ultrasonic echography. Foucault currents, and the analysis of the magnetic field, is complex, and the locating of defects necessitates a precise knowledge of the displacement parameters of this mobile support.

The present invention proposes a method for detecting the thickness variation in the wall of pipes, which enables a signal to be transmitted to the exterior of the pipe, in the case of a buried pipe, in such a way that it is possible to follow the evolution of the parameters measured, which depend upon the thickness, progressively as a recording element advances within the pipe, thus enabling precise locating of defects, and a knowledge of their extent. However, in this method it is only necessary to have a mobile pickup element if one wishes to know the precise place where the defects are located, and the mere presence of the defect, and the extent thereof, can be picked up by fixed elements.

To this end, the present invention has for its object a method in accordance with claim 1.

The essential advantage of this invention resides in its sensitivity, and in the fact that the signal measured is independent of the environment in which the pipe is located. The signal, which is a characteristic voltage of the transverse impedance of the pipe wall, measured by two electrodes, can be transmitted to the exterior of the pipe by a conductor, in such a way that it is possible to make a direct correlation between the progression of the electrodes and the evolution of the signal.

The attached drawing illustrates, diagrammatically and by way of example, different modes of performing the method which is the subject of this invention.

FIG. 1 is an explanatory diagram, illustrating a longitudinal section of a tube on which are entered the characteristic parameters of the method.

FIGS. 2 and 3 are diagrams related to the diagram in FIG. 1.

FIG. 4 is a phase diagram of the signal picked up.

FIG. 8 illustrates, in perspective view, a variant of application of the method according to the invention.

The method is based upon exploitation of the ¢skin effect" which is manifested in any material which is a conductor of electricity, in dependence upon the frequency of the current which passes through it. In the ensuing description, it is considered that the tube T, illustrated in FIG. 1, is normally supplied on its external face with the aid of a current I.

If one considers firstly FIGS. 1 to 3, it will be seen that the current density j and the electrical field E both vary in the same manner, in dependence upon the current frequency.

In fact, the equation which relates to the current density J in dependence upon the depth X in the pipe wall is:

$$j = j_o e^{-x/a}$$

"a" corresponds to the depth of the skin effect and is given by $a = \rho/\pi\mu F$ ($\pi$:resistivity, $\mu$:permeability, and F: frequency)

$j_o$: current density on the external face of the pipe.

This current density decreases rapidly from the external surface to the internal surface of the pipe T, principally for x>a. This variation is given in the table below, which indicates the value of $e^{-x/a}$ for $x_i$=o, a, 2a, 4a, etc.

| $x_i$ | $e^{-xi/a}$ | $e^{-x(i+1)/a}/e^{-xi/a}$ |
|---|---|---|
| 0 | 1.0 | |
| a | 0.368 | 0.368 |
| 2a | 0.135 | 0.368 |
| 4a | 0.018 | 0.135 |
| 8a | $3.35 \cdot 10^{-4}$ | 0.0183 |
| 16a | $1.125 \cdot 10^{-7}$ | $3.35 \cdot 10^{-4}$ |

As regards the corresponding electrical field, it varies in the same manner, being given by the equation:

$$E = jZs$$

$Zs$ : surface impedance $= \omega\rho\mu$ ($\omega$: energizing current pulsation $= 2\pi F$)

As can be seen on the diagram of FIG. 2 which constitutes a graphic representation of the foregoing table, the ratio between the electrical field $E_i$ measured at a suitably selected frequency on the internal face of the pipe T in the part $Q_B$ where the thickness of the wall is reduced and the electrical field in the part $Q_A$ where the thickness is normal, varies strongly in dependence upon this wall thickness. This is the phenomenon which the invention proposes to exploit for showing u the presence of a defect which causes the pipe wall to become thinner.

The signal measured on the internal face of the pipe, and which corresponds to the electrical field on this face, is essentially the result of a resistive component and of an inductive component depending partly on induced parasitic voltages. Thus, only the resistive component is a good measure of the skin effect. Due to this fact, it is necessary that the measuring installation which is intended for operating the method should be designed in such a manner as to reject the part of the signal which is not in phase with the current.

This result can be obtained either with a phase correlation amplifier, or with a frequency and phase response analyzer.

Figure 5:
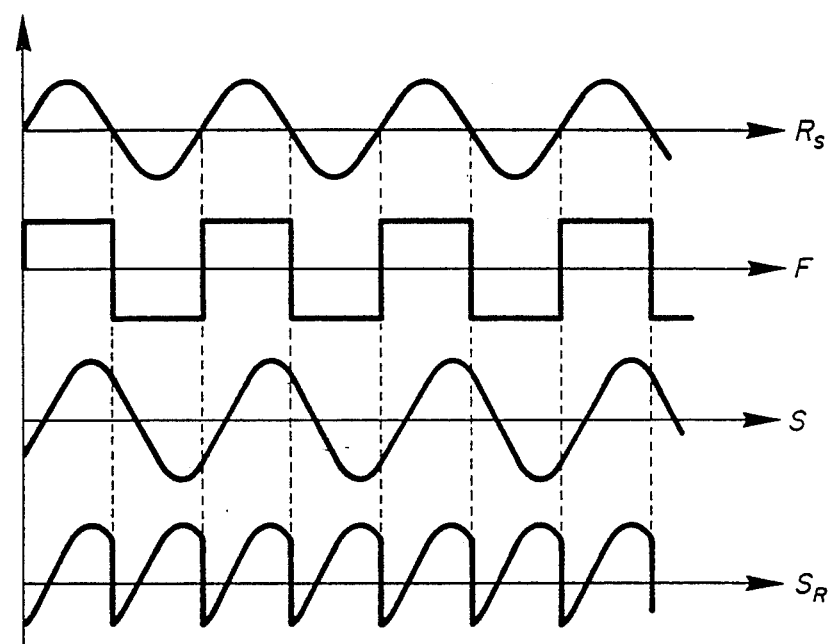
FIG. 5 represents diagrams relating to the treatment of this signal.

By way of example, we will describe an installation which utilizes a phase correlation amplifier. With the aid of FIGS. 4 and 5, we will explain the mode of functioning of such an amplifier, which is utilized as a synchronous demodulator, operating in the following way:

Any signal S (FIG. 4) may be considered as the vector sum of two vectors, one $S_o$ in phase with the reference, and the other $S_{90}$ forming a right angle with this reference. If the demodulator is correlated in phase with the reference signal $R_S$, the rectified signal $S_R$, appearing at the output, will be a function of the vector in phase $S_o$, solely, as can be seen on the diagrams of FIG. 5, where one can see successively the reference signal $R_S$ which enables the formation of a rectangular signal F which constitutes a window through which one rectifies the measured signal S in order to obtain the rectified signal $S_R$.

Figure 6:
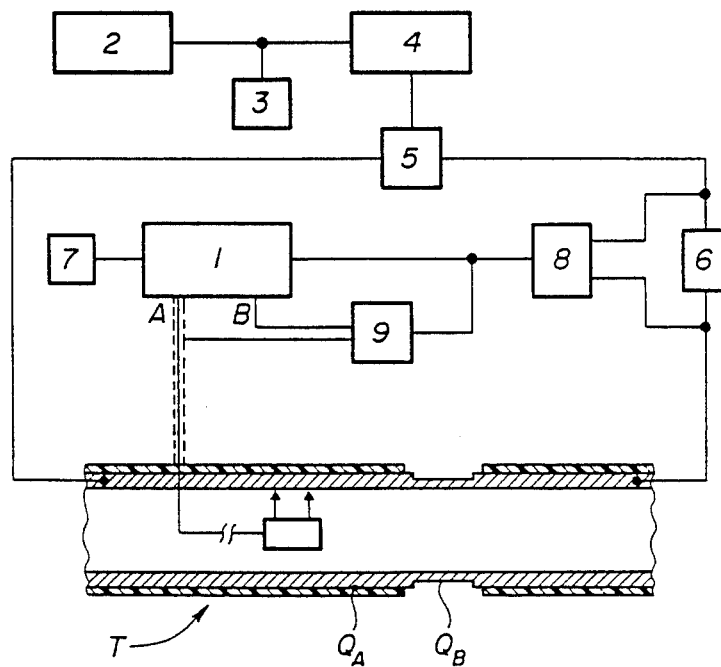
FIG. 6 is a block, diagram of the measuring installation.

The block diagram of FIG. 6 relates, by way of example, to an installation comprising a phase correlation amplifier 1, type PAR 128A, a frequency generator 2, type Wavetek 134, a frequency counter 3, type HP 5300A, a power amplifier 4, type Bruel and Kjaer 2706, a toroidal transformer 5 presenting a transformation ratio of 35 and a maximum secondary current of 20A, a shunt 6 of 10mΩ with a maximum current of 10A, a voltmeter 7, type Solartron 7040, a low-power amplifier 8, type Levell TA 605, and a switching box 9. The frequency may vary from 3 to 1000 Hz, with a maximum current of 10A.

The functioning of this installation consists in supplying the transformer 5 from the generator 2 and from the amplifier 4, so as to produce the current intended for supplying the pipe T and for measuring the voltage at the terminals of the shunt 6. This voltage, characteristic of the energizing current, is first of all amplified 10-fold by the amplifier 8 in order to obtain a sufficient amplitude, and is then brought to the reference input of the phase correlation amplifier 1. The output of this amplifier 8 may also be connected to the measuring input of the phase correlation amplifier 1, via the intermediary of the switching box 9. This last mode of connection can enable the measuring and the control of the current amplitude, as well as the phase control.

The resistive component of the signal on the pipe is then measured by connecting the measuring points at the differential inputs A and B of the phase correlation amplifier 1, and by only measuring the in-phase component of the signal. The connection must be made in such a manner as to measure only the internal field, which signifies that in order to exit from the tube, it is necessary to use a coaxial cable which is insensitive to the external magnetic flux.

The measuring, itself, of the signal picked up on the pipe T after it has been supplied with the reference signal, may be performed in three different ways.

Figure 7:
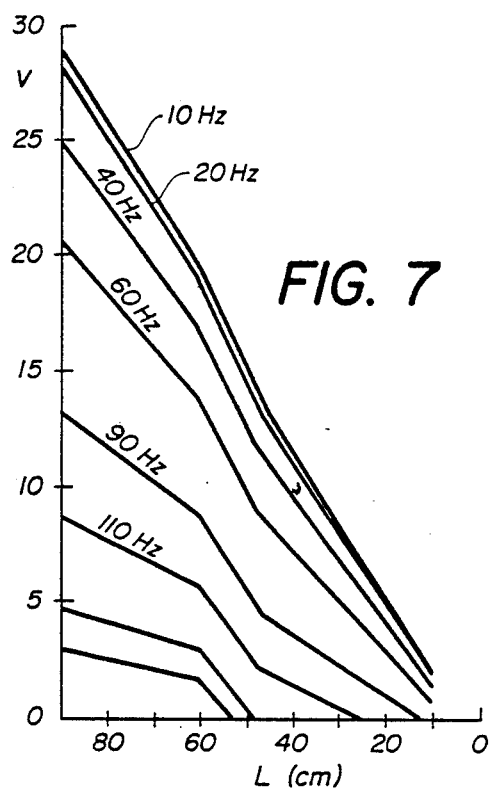
FIGS. 7 and 8 are diagrams relating to the modes of working this method.

One of the measuring points may be fixed on the internal face of the pipe T, and the other point may be displaced longitudinally on this same face. This displacement may be repeated several times, varying, at each movement of the mobile point, the supply current frequency. In the case of the pipe section T on which a reduction of thickness $Q_B$ has been produced, the rest of the pipe T presenting a constant thickness $Q_A$, the diagram of the voltage V in dependence upon the distance L separating the two points from one another is given by FIG. 7. It can be seen that the defect becomes particularly visible in the region of 100 Hz, for the pipe examined. This measurement makes it possible to determine at one and the same time the extent, and the longitudinal position, of the defect.

Figure 8:
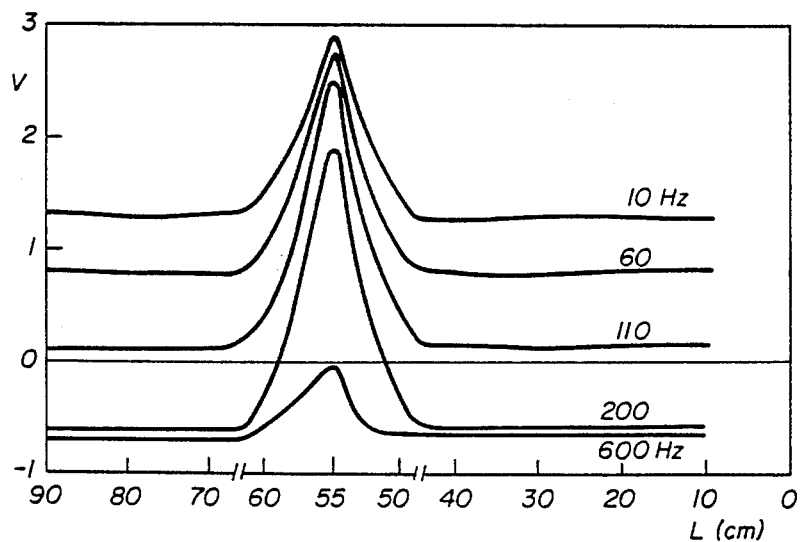

According to another method of operating this measurement process, the two points for measuring the signal on the internal face of the pipe T are maintained at a fixed distance from one another, and are displaced together along this internal face. This displacement may be repeated on one and the same section of pipe, varying the supply current frequency, which also constitutes the reference signal. The presence of the defect immediately becomes apparent on the diagram of FIG. 8, in the form of a peak which varies in dependence upon the frequency, this peak being, in this example, the biggest one between 100 and 200 Hz. As in the preceding case, the peak is characteristic of the extent and the position of the defect, along the pipe.

The inconvenience of these solutions originates from the necessity of displacinq at least one of these pickup points of the signal in the interior of the tube. This means that, in the case of a buried pipe, it is necessary to place the mobile pickup point or points on a transport member which, obviously, must be introduced into the pipe at the time of measuring, and subsequently withdrawn. Such members, intended for displacement within a tubular conduit, are already in existence, but it would also be interesting to have a solution based upon the principle of the skin effect, to which the invention has recourse, but enabling the measuring of the signal with the aid of fixed points. In journal face of the pipe, separated by a given distance, and one can connect them to the exterior b assembly of two conductors arranged in the coaxial mode connected to exterior sensor 11, in such manner as not to pick up the external magnetic flux, and to which a measuring installation is connected. The electrical field existing on the internal face between these two points is then measured in dependence upon the frequency.

In this variant for pickup of the signal, the curves recorded, in dependence upon the frequency sweep, will enable the detection of the defects in the thickness of the pipe, by comparing the curve to a series of curves traced with the aid of a computer and obtained by causing the unknown parameters to vary, that is to say the non-geometrical parameters such as the resistivity $\rho$ and the permeability $\mu$. If one arbitrarily fixes the depth of the corrosion, the length of the corroded parts is likewise an unknown, and thus will also constitute one of the parameters in which it will be necessary to cause variations.

The comparison of these curves, calculated with the curve measured, will then make it possible to ascertain the presence of defects and, within certain limits, to estimate the extent thereof. On the other hand, the location of the defect or defects between the two measuring points cannot, in this case, be determined. This disadvantage is compensated by the fact that this method of picking up the signal does not necessitate mobile electrodes in the interior of the pipe, which obviously constitutes a simplification in the mode of operating. In the case of new installations, the pipes may be provided with internal electrodes for pickup of the signal, connected for example to a measuring station by a cabling system. In existing installations used for the urban distribution of gas, for example, it is possible to gain access to the interior of the pipelines by the different branch connections to dwellings. These same branch connections can be used for introducing mobile electrodes into the interior of the pipe, in accordance with the pickup modes described precedingly.

As indicated hereinabove, the preceding description deals with the case where the measuring is performed in the interior of the tube. If one wishes to perform the measuring in the exterior of the tube, the energization must be performed in the interior of the tube, so that the skin effect can manifest itself on the internal face.

However, in the case of measurement of the electrical field in dependence upon the frequency between two fixed points, and of the comparison of the curve obtained with a series of curves traced with the aid of a computer and obtained by causing the unknown non-geometrical parameters to vary, as indicated hereinabove, it is then possible to utilise this same method by performing the measuring of the same side of the pipe as that by which one is performing the supplying. The signal measured then, in fact, will be that of the evolution of the electrical field in dependence upon the current frequency sent through the pipe.

Consequently, it becomes possible to perform measurements on buried pipes, by simply coming into contact with the external face of the wall of these pipes. We are now going to describe, in slightly greater detail, different manners of proceeding with this comparison operation. It is assumed that one knows all the geometrical parameters of the pipe, with the exception of the modifications to these parameters which are the result of corrosion. On the other hand, the electrical parameters are unknown, due to the fact that one knows neither the temperature nor the electrical properties of the material from which the tube is made, nor the influences of its environment.

The mathematical model which is used is based upon three formulae, suitable for calculating the impedance of the pipe (1) with direct current or with very low frequency (<1HZ), (2) wit high frequency for which the skin effect is total, that is to say, that it manifests itself completely within the thickness of the pipe wall, and (3) with intermediate frequency, where the skin effect is produced beyond the thickness of the pipe wall. These three formulae are given hereinafter, in the aforesaid order:

$$E_{DC} = \rho \frac{L_o}{S_a} = \rho \frac{L_o}{\pi(r^2 - q^2)} \quad (1)$$

wherein:

$L_o$ represents the length of the pipe considered $S_a$ represents its cross section with r the exterior radius and q the interior radius $\rho$ represents the resistivity $$R_{AC} = \frac{L_o}{2r} \sqrt{\frac{\rho\mu F}{\pi}} \quad (2)$$

wherein:

$\rho$ is the resistivity $\mu$ is the permeability

F is the frequency.

The third formula gives the impedance per unit of length Z, taken from H.B. Duright: "A Precise Method of Calculation of Skin Effect in Isolated Tubes":

$$Z'/R_{DC} = \frac{jmr}{2} \frac{(r^2 - q^2)}{r^2} \frac{\left[ (ber\, mr + j\, bei\, mr) + \frac{(C + jD)}{(A + jB)} (ker\, mr + j\, kei\, mr) \right]}{\left[ (ber'mr + j\, bei'mr) + \frac{(C + jD)}{(A + jB)} (ker'mr + j\, kei'mr) \right]} \quad (3)$$

with $$\frac{C + jD}{A + jB} = -\frac{(ber'mq + j\, bei'mq)}{(ker'mq + j\, kei'mq)}$$

wherein:

$R_{DC}$ is the resistance of the pipe to the direct current
j the imaginary unit ($\sqrt{-1}$)
$m = \sqrt{2\pi f \mu / \rho}$; the depth d of the conventional skin effect is related to m by $m = \sqrt{2}/d$
f the frequency
$\mu$ the permeability of the conductor
$\rho$ the resistivity of the conductor
r the external radius of the pipe
q the internal radius of the pipe
ber and bei the real and imaginary parts of the Kelvin function of the first type
ker and kei the real and imaginary parts of the Kelvin function of the second type, all four of the order of zero.
ber', bei' and kei' the derivatives of the corresponding Kelvin functions.

The known geometrical parameters are therefore $L_o$, r and q, those which are unknown are $\rho$ and $\mu$, as well as the external radius $\tau$ of the pipe in the corroded zones.

Various different approaches may be envisaged for making and analysing the correlation between the longitudinal impedance measured in dependence upon different supply current frequencies and the mathematical model. By way of example, there could be mentioned three different approaches which are capable of solving this problem.

In a first example, it is assumed that the considered pipe section is free from corrosion, which implies the perfect application of the model.

The equation (1) then enables one to calculate a value of $\rho$, corresponding to an uncorroded pipe. Then one has recourse to the equation (3) for calculating, for each frequency $f_i$ for which $Z'/R_{DC} > 1$, the value of the magnetic permeability $\mu_i$.

If the successive values of $\mu_i$, thus calculated starting from this $\rho$, are constant, or follow a law corresponding to the magnetic permeability of the steel used for manufacturing the pipe, the initial supposition that this pipe is not corroded is thus found to be confirmed. In contrary case, one can conclude that the pipe is corroded between the two measuring points.

According to a second example, it is assumed that the pipe comprises a corroded zone of determined qeometry, for example a defect extending in ring-shaped form on the external face of the pipe, whose width is unknown and concerning which it is assumed that it affects half the thickness of its wall:

One then adapts the mathematical model to these new conditions. The correlation and its interpretation comprise, in this case, two variants, a simplified variant which is less precise, and a high-precision variant which is more complicated.

In the case of the first of these variants, one utilizes the equation (2) for determining the product $\rho \mu$, it being given that the value of $R_{AC}$, relative to the total skin effect, is practically independent of the presence of corrosion defects.

With the aid of the formula (3), one searches, with the aid of a sweeping loop, for a value of $\mu$ (o) which corresponds to an impedance value measured at a determined frequency, selected such that the skin effect is restricted to a wall thickness corresponding to the thickness left remaining by the supposed corrosion (50%) with annular distribution. With the aid of a second sweeping loop, which may contain the preceding one, and with the aid of the formula (3) adapted in dependence upon the supposed geometry of the defect, one determines the width of the supposed corroded zone, which corresponds to the width for which one finds again the value of the measured longitudinal impedance.

The disadvantage of this method originates from the fact that the determination of the product $\rho \mu$, at a relatively high frequency, causes one to take into account a value of $\mu$ which may already have been influenced by the frequency.

The utilisation of one single frequency for the loop on $\mu$ only makes use of part of the information available. Finally, the fact of arbitrarily basing the investigation on a certain type of corrosion defect does not take into account the fact that the corrosion of the pipe may be of another type.

According to a variant of this mode of correlation, one utilises a series of mathematical models corresponding to various different types of corrosion attack. Moreover, this correlation must take into account impedance variations in dependence upon the frequency from the time when the influence of the skin effect appeared, whilst avoiding taking into account the result of the measurements corresponding to the high frequencies, in such a manner as to reduce the influence of the variation of $\mu$ in dependence upon the frequency.

Figure 9:
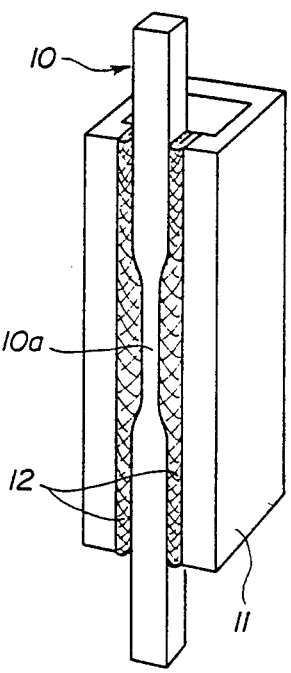

The variant illustrated by FIG. 9 shows an application of the process according to the invention, for the detection of the propagation of cracks on a traction test sample 10. The zone 10a of the test sample in which the cracks are occurring, in consequence of the traction, is integrated within the wall of a tubular metallic casing 11, with interposition of a deformable element, such as a copper braiding 12, folded up on both sides of the test sample 1 and serving to establish the electrical connection between the test sample 10 and the tubular casing 11, without this casing participating in the traction stress exerted upon the test sample.

When the method according to the invention is being operated, the casing 11, with its test sample 10, are supplied via one of the internal or external faces. The electrical field is measured on the other face. It being given that this field depends upon the transversal impedance, when a crack appears on the test sample, and progresses, the measured electrical field increases for a higher frequency, to a frequency limit which is the higher, the deeper the crack is.

We claim:

1. Method for detecting thickness variations in a wall of a tubular body which is made of an electrically conducting material, comprising:

supplying a reference alternating current to one face of the wall of this tube measuring, on the other face, a signal which represents an evolution of a characteristic voltage of an electrical field between two electrodes which are spaced apart longitudinally from one another, rejecting a part of the measured signal which is out of phase with the reference alternating current, and varying at least one of the parameters from the group consisting of the distance between the electrodes, the longitudinal position of the two electrodes along the aforesaid body, and the frequency of the energization current.

2. A method as in claim 1, wherein said reference alternation current has a frequency less than 100 hz.

3. Method for detecting thickness variations in a wall of a tubular body which is made of an electrically conducting material, comprising the steps of:
    (a) providing a mathematical model for calculating an impedance of the tubular body using excitation currents within at least two predetermined ranges of frequencies in which the skin effect of the current is substantially different,
    (b) supplying a reference alternating current to one face of the wall of said tubular body,
    (c) varying a frequency of this reference current according to said predetermined ranges of frequencies,
    (d) measuring on one face of this wall between two electrodes which are spaced apart longitudinally from one another, signals which represent characteristic voltages of electrical fields at respective frequencies of the reference current, and rejecting a portion of the measured signals which is out of phase with the reference alternating current,
    (e) arbitrarily assuming a value for a thickness variation in said wall,
    (f) solving a first equation of said mathematical model with one of said measured signals corresponding to a frequency within a first of said ranges and said assumed value of thickness variation, in order to identify an unknown parameter,
    (g) solving a second equation of said mathematical model with the other of the measured signals corresponding to frequencies of the second of said ranges and said identified parameter in order to identify another unknown parameter,
    (h) checking an evolution of this other parameter in order to determine if said value of thickness variation is correct or not, and
    (i) if not, repeating steps e) to h) after choosing another value of thickness variation, and repeating this step until said thickness variation proves to be correct.

4. A method as in claim 1 wherein said reference alternation current has a frequency less than 100 hz.

* * * * *